(12) United States Patent
Dasbach (10) Patent No.: US 10,159,803 B2
(45) Date of Patent: Dec. 25, 2018

(54) DRUG DELIVERY DEVICE WITH NEEDLE PROTECTION

(71) Applicant: Sanofi-Aventis Deutschland GmbH, Frankfurt am Main (DE)

(72) Inventor: Uwe Dasbach, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 14/766,210

(22) PCT Filed: Feb. 6, 2014

(86) PCT No.: PCT/EP2014/052312
§ 371 (c)(1),
(2) Date: Aug. 6, 2015

(87) PCT Pub. No.: WO2014/122206
PCT Pub. Date: Aug. 14, 2014

(65) Prior Publication Data
US 2015/0374927 A1 Dec. 31, 2015

(30) Foreign Application Priority Data
Feb. 8, 2013 (EP) .................................. 13154690

(51) Int. Cl.
*A61M 5/32* (2006.01)
*A61M 5/24* (2006.01)
*A61M 5/315* (2006.01)

(52) U.S. Cl.
CPC .......... *A61M 5/3202* (2013.01); *A61M 5/326* (2013.01); *A61M 5/24* (2013.01);
(Continued)

(58) Field of Classification Search
CPC .. A61M 2005/3267; A61M 2005/3254; A61M 2005/3247; A61M 5/3202;
(Continued)

(56) References Cited

U.S. PATENT DOCUMENTS

| 533,575 A | 2/1895 | Wilkens |
|---|---|---|
| 5,226,895 A | 7/1993 | Harris |

(Continued)

FOREIGN PATENT DOCUMENTS

| CN | 102639170 A | 8/2012 |
|---|---|---|
| EP | 0937471 A2 | 8/1999 |

(Continued)

*Primary Examiner* — Emily Schmidt
*Assistant Examiner* — Alexandra Lalonde
(74) *Attorney, Agent, or Firm* — McCarter & English, LLP (57) ABSTRACT

A drug delivery device for dispensing a dose of a medicament may include an elongated housing extending in an axial direction to accommodate a cartridge containing a medicament to be dispensed, wherein the housing being further adapted to detachably support a needle assembly at a distal end thereof, a drive mechanism comprising a piston rod to operably engage with a piston of the cartridge, a protecting sleeve slidably attached to the distal end of the housing to enclose the needle assembly in a distal stop position and to expose the needle assembly in a retracted proximal stop position, and an interlocking member operably engaged with the protecting sleeve and being axially displaceable relative to the housing between a locking position, in which the protecting sleeve is locked to the housing, and a release position, in which the protecting sleeve is axially displaceable relative to the housing.

19 Claims, 3 Drawing Sheets

(52) U.S. Cl.
CPC ... *A61M 5/3155* (2013.01); *A61M 2005/3247* (2013.01); *A61M 2005/3267* (2013.01)

(58) Field of Classification Search
CPC .. A61M 5/3205; A61M 5/322; A61M 5/3243; A61M 2005/208; A61M 2005/2073; A61M 5/24; A61M 5/31525; A61M 5/31536; A61M 5/31541; A61M 5/31543; A61M 5/31551; A61M 5/31585; A61M 5/31593; A61M 5/326; A61M 2005/20; A61M 2005/2013; A61M 2005/206; A61M 5/3219; A61M 5/3272; A61M 5/3271; A61M 5/2033
See application file for complete search history.

(56) References Cited

U.S. PATENT DOCUMENTS

| | | |
|---|---|---|
| 5,261,894 A | 11/1993 | Smith et al. |
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,437,647 A | 8/1995 | Firth et al. |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,371,939 B2 * | 4/2002 | Bergens ............ A61M 5/2033 604/156 |
| 6,899,698 B2 | 5/2005 | Sams |
| 6,936,032 B1 | 8/2005 | Bush, Jr. et al. |
| 7,241,278 B2 | 7/2007 | Moller |
| 7,465,289 B2 | 12/2008 | Marshall |
| 9,033,935 B2 | 5/2015 | Bostrom |
| 9,833,579 B2 | 12/2017 | Pedersen et al. |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2005/0261634 A1 * | 11/2005 | Karlsson ............ A61M 5/20 604/197 |
| 2005/0273061 A1 * | 12/2005 | Hommann ......... A61M 5/2033 604/198 |
| 2006/0129105 A1 | 6/2006 | Hommann et al. |
| 2006/0153693 A1 | 7/2006 | Fiechter et al. |
| 2006/0167412 A1 * | 7/2006 | Marshall ............ A61M 5/2033 604/110 |
| 2008/0177238 A1 | 6/2008 | Follman et al. |
| 2009/0275916 A1 | 11/2009 | Harms et al. |
| 2009/0326477 A1 * | 12/2009 | Liversidge ............ A61M 5/326 604/198 |
| 2015/0320939 A1 * | 11/2015 | Beek ................ A61M 5/31525 604/193 |

FOREIGN PATENT DOCUMENTS

| | | |
|---|---|---|
| EP | 0937476 A2 | 8/1999 |
| JP | H09-501085 A | 2/1997 |
| JP | 2006-526446 A | 11/2006 |
| JP | 2013-534164 A | 9/2013 |
| WO | 9938554 A1 | 8/1999 |
| WO | 0110484 A1 | 2/2001 |
| WO | 2005113039 A1 | 12/2005 |
| WO | 2007077463 A1 | 7/2007 |

* cited by examiner

DRUG DELIVERY DEVICE WITH NEEDLE PROTECTION

CROSS REFERENCE TO RELATED APPLICATIONS

The present application is a U.S. National Phase Application pursuant to 35 U.S.C. § 371 of International Application No. PCT/EP2014/052312 filed Feb. 6, 2014, which claims priority to European Patent Application No. 13154690.5 filed Feb. 8, 2013. The entire disclosure contents of these applications are herewith incorporated by reference into the present application.

FIELD OF INVENTION

The present invention relates to a drug delivery device to dispense or to inject a predefined dose of a medicament from a cartridge. The drug delivery device is generally manually operable and allows for individually setting and/or dispensing of a dose of the medicament.

BACKGROUND

User operated drug delivery devices are as such known in the prior art. They are typically applicable in circumstances, in which persons without formal medical training, i.e., patients, need to administer an accurate and predefined dose of a medicament, such as heparin or insulin. In particular, such devices have application, where a medicament is administered on a regular or irregular basis over a short-term or long-term period.

In order to accommodate with these demands, such devices have to fulfil a number of requirements. First of all, the device must be robust in construction, yet easy to use in terms of handling and in understanding by the user of its operation and the delivery of the required dose or medicament. The dose setting must be easy and unambiguous. Where the device is to be disposable rather than reusable, the device should be inexpensive to manufacture and easy to dispose.

Drug delivery devices, in particular injection devices, such like pen-type injectors are designed and adapted for self-medication, where a user or patient, e.g. suffering a chronic disease regularly utilises the drug delivery device. With such injection devices, a disposable injection needle is for instance to be removably attached to a distal dispensing end of the device. At least for injecting of a dose of the medicament, the free and tipped end of an injection needle may be at least temporally exposed to the environment or to the user. An exposed needle always represents a certain danger to health. The patient himself or other persons may be therefore exposed to an increased risk of a needle stitch.

There already exist safety shield systems for such pen needles as for instance described in US 2008/0177238 A1. There, the safety shield system is integrated in a disposable needle assembly, which after a single use is to be discarded due to hygienic reasons. Since the safety shield system is rather elaborate such safety needle assemblies are comparatively expensive compared to non-shielded disposable needle assemblies conventionally to be used with pen-type injectors.

It is therefore an object of the present invention to provide a drug delivery device with an improved protection mechanism to avoid inadvertent needle stitches. It is a particular aim of the present invention to provide a protection mechanism for an injection device, which allows to make use of conventional disposable injection needles, especially with pen-type injectors. Moreover, the protection mechanism should be particularly applicable to all-mechanically implemented drug delivery devices exclusively operated and driven by a manual handling of a user. The protection mechanism is particularly adapted for repeated use with a series of injection needles.

SUMMARY

In a first aspect the invention relates to a drug delivery device for dispensing of a dose of a medicament. The device comprises an elongated housing extending in an axial direction to accommodate a cartridge containing a medicament to be dispensed by the drug delivery device. The housing of the drug delivery device is furthermore adapted to detachably support a needle assembly at a distal end thereof.

In the present context, the distal end denotes the axial end portion of the drug delivery device which points towards the patient whereas the oppositely oriented proximal direction faces away from the patient. Typically, the distal end of the drug delivery device serves as an injection end to dispense a predefined amount of the medicament whereas the proximal end of the drug delivery device comprises at least one actuation member allowing to set and/or to dispense a respective dose of the medicament.

The drug delivery device further comprises a drive mechanism at least comprising a piston rod to operably engage with a piston of the cartridge. Typically, the cartridge comprises a tubular-shaped barrel sealed in proximal direction by means of the piston slidably disposed therein. When the cartridge is assembled and fixed in the housing, the distal end of the piston rod, typically featuring a pressure foot abuts and/or engages with the proximal end face of the cartridge to exert distally-directed pressure thereon.

The drug delivery device is typically implemented as a disposable device, which is to be discarded in its entirety when the content of the cartridge has been used up. With such a disposable device, the cartridge is non-removable disposed inside the device. With disposable drug delivery devices, the housing of the device is sealed to impede access to the cartridge disposed therein.

However, in an alternative embodiment, the drug delivery device may be designed as a reusable device. Here, the housing of the device is intended to be opened or to disassembled in order to provide access to the cartridge disposed therein. With a reusable device, an empty cartridge is replaceable by a new one. Moreover, the drive mechanism may then typically provide a reset function.

By means of the distally-directed displacement of the piston rod relative to the barrel of the cartridge, the piston of the cartridge can be displaced accordingly, thereby expelling a predefined amount of the medicament through an injection needle being in fluid transferring contact with the interior volume of the cartridge. Typically, the injection needle comprises a distal and a proximal-tipped end. With its proximal end the needle is adapted to penetrate a pierceable seal or septum provided at a distal end section of the cartridge.

The drug delivery device further comprises a protecting sleeve slidably attached to the distal end of the housing to enclose or to shield the needle assembly when attached to the distal end of the housing of the drug delivery device. The protecting sleeve is slidably displaceable between a distal stop position and a retracted proximal stop position. In its distal stop position the protecting sleeve is adapted to entirely surround, to enclose and/or to effectively shield the needle assembly, in particular its distally-located tipped end. In the retracted proximal stop position, in which the protecting sleeve is displaced relative to the housing in proximal direction, the needle assembly, at least its distal-tipped end is exposed in order to enter biological tissue for deposition of the medicament therein.

The drug delivery device further comprises an interlocking member operably engaged with the protecting sleeve. Also the interlocking member is axially displaceable relative to the housing. In particular, the interlocking member is axially displaceable between a locking position and a release position. Mutual engagement between the interlocking member and the protecting sleeve is such, that the protecting sleeve is locked to the housing when the interlocking member is in its locking position. Furthermore, the protecting sleeve is axially displaceable relative to the housing, in particular between the distal stop position and the retracted proximal stop position when the interlocking member is in its release position.

In this way, a twofold axial displacement of protecting sleeve and interlocking member can be provided, such that an axially-directed relative displacement of protecting sleeve and housing can be selectively locked or released by the interlocking member, which itself is also axially displaceable relative to the housing between a locking position and a release position.

The mutual engagement of the interlocking member and the protecting sleeve together with the axially-directed displacement of interlocking member and protecting sleeve relative to the housing provides an intuitive approach for releasing the protecting sleeve as well as for displacing the protecting sleeve relative to the housing for exposing the needle assembly. Preferably, releasing of the protecting sleeve by means of an axially-directed displacement of the interlocking member relative to the housing as well as displacing of the released protecting sleeve relative to the housing can be obtained and induced by a single movement of the interlocking member relative to the housing. Therefore, the protection mechanism provided by the protecting sleeve and the interlocking member allows for a very intuitive, straightforward and easy handling for dispensing of a dose of the medicament.

According to an embodiment, the interlocking member comprises a gripping sleeve slidably attached to the housing. Hence, the interlocking member is also designed as a sleeve arranged around the outer circumference of the elongated housing of the drug delivery device. The interlocking member is particularly adapted to be gripped by a hand of a user when utilizing the drug delivery device.

Since the interlocking member provides a grip, the entire drug delivery device can be taken and gripped by the interlocking member. In a typical application scenario, the drug delivery device is to be pressed in distal-direction against the skin of a patient. Here, the interlocking member, e.g. in form of the gripping sleeve provides axial force transmission to axially displace the interlocking member relative to the housing in distal-direction for establishing a release configuration for the protecting sleeve.

In a second and subsequent step, distally-directed force acting on the interlocking member may be transferred via the interlocking member into a distally-directed displacement of the needle assembly relative to the protecting sleeve.

Since the interlocking member serves as a gripping sleeve, a user of the device may intuitively take and grip the entire drug delivery device by means of the interlocking member in such a way, that the interlocking member is axially displaced relative to the housing of the drug delivery device during a dispensing or injection procedure, in which the entire device is pressed in distal direction against the user's skin. Since it is the interlocking member itself which serves to receive a distally directed driving force exerted by a user, release of the protecting sleeve as well as a relative displacement between the protecting sleeve and needle assembly can be derived from a distally directed exertion thrust against the patient's skin while gripping of the interlocking member of the drug delivery device.

In a further embodiment, the locking position of the interlocking member coincides with a proximal stop position of the interlocking member. Hence, by displacing the interlocking member in proximal-direction relative to the housing, the interlocking member reaches a locking position, in which the protecting sleeve is axially fixed or axially secured relative to the housing. Furthermore, the release position of the interlocking member coincides with a distal stop position of the interlocking member. Here, the interlocking member is displaceable in distal-direction relative to the housing until it reaches a distal stop position that coincides with the release position of the interlocking member, in which the protecting sleeve is released and is free to move in axial-direction, preferably in proximal direction relative to the housing.

In a typical application scenario, the protecting sleeve is positioned against the skin of the patient. Then, by gripping the interlocking member and by applying distally-directed thrust or a driving force onto the interlocking member, said interlocking member is distally displaced relative to the housing, thereby releasing the protecting sleeve. Once the distal stop position of the interlocking member has been reached, further and continuous application of a distally-directed thrust or force may then advance the needle assembly in distal-direction relative to the protecting sleeve, thereby exposing the needle assembly from a distal end face of the protecting sleeve.

Once the interlocking member has reached the distal stop position any further force effect acting on the interlocking member in distal-direction may be transferred to the housing of the drug delivery device, which may then displace in distal-direction together with the needle assembly mounted thereon relative to the protecting sleeve. In other words, during such a further displacement, the protecting sleeve experiences a proximally-directed displacement relative to the distally advancing housing of the drug delivery device, thereby exposing the distal end of the tipped needle assembly.

According to another embodiment, the interlocking member is displaceable in distal-direction relative to the housing against the action of a locking spring element. By means of the locking spring element, the interlocking member can be returned into an initial proximal stop position as soon as an externally applied and distally-directed force effect drops below a predefined threshold. In a typical application scenario, the interlocking member is displaceable in distal-direction relative to the housing under the effect of a force applied by a user when pressing the drug delivery device against a patient's skin in distal-direction. As soon as the drug delivery device is no longer pushed against a skin portion of a patient, the locking spring element serves to return the interlocking member into its proximal stop position.

Moreover and according to another embodiment, the protecting sleeve is displaceable in a proximal-direction relative to the housing against the action of a protecting spring element. In other words, it is the housing of the drug delivery device, which is displaceable in distal-direction relative to the protecting sleeve against the action of the protecting spring element. In this way, exposing of the distal end of the needle assembly by means of a mutual axial displacement of protecting sleeve and housing is to be conducted under the action of the protecting spring element.

As soon as a respective distally-directed force is no longer applied to the drug delivery device and/or to the interlocking member, e.g. implemented as a gripping sleeve, the protecting spring element serves to return the protecting sleeve into its distal stop position to enclose and to shield the needle assembly after termination of an injection procedure.

According to a further embodiment, the spring constant of the locking spring element is substantially smaller than a spring constant of the protecting spring element. Preferably, both spring elements are compressible in distal direction and are further arranged in a sequential order. Since the protecting spring element and the locking spring element are differently dimensioned, an initial force action in distal-direction to the interlocking member may initially displace the interlocking member from its proximal locking position into its distal release position before the protecting spring element is substantially compressed.

In this way, a two-step or twofold protection mechanism can be provided, wherein in a first step the protecting sleeve is distally displaced relative to the housing against the action of the locking spring element. When a corresponding distal stop position of the interlocking member has been reached, the protecting sleeve is effectively released and may then be displaced in axial-direction relative to the housing against the action of the protecting spring element. At the end of a typical dispensing procedure, where the drug delivery device is to be removed from the skin of the patient, the same relative displacement of protecting sleeve and interlocking member may occur in reverse order.

As soon as a distally-directed holding or dispensing force drops below a predefined threshold, the protecting spring element may be operable to return the protecting sleeve into its distal stop position to shield and to enclose the needle assembly. Then, in a further step, the interlocking member can be returned into its proximal locking position under the action of the locking spring element.

In another embodiment, the locking spring element axially extends between a proximally-located receptacle of the interlocking member and a radially outwardly extending flange portion of the housing of the drug delivery device. In this way, the interlocking member can be axially biased against the housing by means of the locking spring element.

In a further embodiment, the protecting spring element may extend between a distal end section of the protecting sleeve and a radially outwardly extending flange portion of the housing. Typically, the protecting spring element is arranged inside the protecting sleeve and may axially abut with a radially outwardly extending flange portion or rim provided at a distal end of a cartridge holder of the drug delivery device. In typical embodiments, the protecting sleeve comprises an axial extension large enough to cover the entirety of the needle assembly when mounted on a distal end of the housing, hence to a cartridge holder thereof.

Protecting sleeve and interlocking member are typically axially separated from each other. Typically, the interlocking member is of substantially tubular-shape and substantially encloses a major portion of a proximal housing component of the drug delivery device, which is typically denoted as a body of the drug delivery device that serves to accommodate the device's drive mechanism. The protecting sleeve however, is positioned at a predefined axial distance from the interlocking member in order to effectively protect and shield the needle assembly mounted on the distal end, hence on a cartridge holder section of the housing of the drug delivery device.

According to another embodiment, the protecting sleeve comprises at least one extension extending in proximal-direction and having a radially outwardly extending protrusion. The operable engagement between the protecting sleeve and the interlocking member is typically provided by the at least one extension. By way of the extension, the protecting sleeve can be selectively fixed and immobilised relative to the housing by means of an axial displacement of the interlocking member.

It is particularly due to the radially outwardly extending protrusion that the extension can be radially bent or radially displaced by means of an axial displacement of the interlocking member relative to the housing and/or relative to the at least one extension. Typically, by means of a radial displacement, either due to a pivoting or due to an elastic deformation, the protecting sleeve may selectively engage or disengage with the housing of the drug delivery device.

In a further embodiment, the extension of the protecting sleeve extends radially between the housing and the interlocking member slidably disposed on the housing. By arranging the extension substantially inside the sleeve-like interlocking member, the comparatively filigree extension can be mechanically protected. Moreover, its functionality can be effectively concealed and a manipulation of the at least one extension from outside the device can be effectively prevented.

Additionally, by having the extension arranged radially between the housing and the interlocking member, the extension can be mechanically deformed or radially displaced by way of a relative axial displacement of housing and interlocking member.

According to another embodiment, the at least one extension axially abuts with a stepped portion of the housing and is radially constrained by the interlocking member when the interlocking member is in the locking position. In said abutment configuration with the housing, the extension is axially fixed to the housing and thereby prevents an axially-directed relative displacement of the housing and the protecting sleeve. Since the interlocking member radially constrains the extension, said extension remains in the axial abutment configuration with the housing. In this way, the protecting sleeve remains in its distal stop position to effectively enclose or to effectively shield the needle assembly.

According to another embodiment, the at least one extension is radially released to pass by said stepped portion of the housing when the interlocking member is in the release position. By a displacement of the interlocking member in distal direction relative to the housing, the radially outwardly extending protrusion of the at least one extension is no longer radially inwardly constrained by e.g. an inward-facing sidewall portion of the interlocking member. Either due to a pretension or by means of mutually corresponding surface structures, the at least one extension of the protecting sleeve may become subject to a radially outwardly-directed evasive movement allowing the at least one extension to pass by the stepped portion of the housing. In this way, the protecting sleeve can be displaced in axial direction relative to the housing in order to at least temporally expose the needle assembly therefrom.

In a further embodiment, the protrusion of the at least one extension of the protecting sleeve comprises at least one inclined ramp portion to engage with a correspondingly-shaped ramp portion or with a recess provided on the outer circumference of the housing and/or on the inside-facing sidewall portion of the interlocking member.

By means of mutually engaging ramp portions, application of distally or proximally-directed displacing forces acting between the at least one extension, the interlocking member and/or the housing may inherently support or trigger a radially-directed evasive movement of the extension for releasing or interlocking the same from or to the housing.

In a further embodiment, the protrusion of the at least one extension comprises a proximal end face to axially abut with a correspondingly shaped radially outwardly extending rim of the housing. By means of the proximal end face, to axially abut with the rim of the housing, the protecting sleeve can be axially fixed relative to the housing when reaching the retracted proximal stop position. In this way, proximally directed displacement of the protecting sleeve relative to the housing can be confined.

According to another embodiment, the protrusion of the at least one extension is axially guided in a slit or in a groove of the interlocking member. At least when reaching the distal release configuration, the radially outwardly extending protrusion of the extension may engage with an axially extending slit or groove of the sleeve-like interlocking member. Moreover, also in the interlocking position, the inward-facing sidewall portion of the interlocking member may comprise a slit or groove to receive the radially outwardly extending protrusion of the at least one extension. In this way, a rotational interlock between interlocking member and extension, hence between interlocking member and protecting sleeve can be effectively provided.

In a further embodiment, the protecting sleeve comprises at least two diametrically oppositely located and symmetrically designed extensions adapted to mate with correspondingly shaped step portions of the housing and featuring respective inclined ramp portions. Here, it is even conceivable, that the stepped portion and/or the radially outwardly extending rim of the housing extends around the entire circumference of the substantially tubular-shaped housing. In this way, a rotation invariant arrangement of extensions and housing can be obtained.

According to another embodiment, the distal end of the protecting sleeve comprises a receptacle to removably receive a protective needle cap of the needle assembly. In preferred embodiments, a conventional and non-shielded needle assembly comprising a needle hub to be attached to a distal end of a cartridge holder can be assembled to the distal end of the protecting sleeve by making use of a protective cap covering the needle assembly. For this purpose, the protective cap and the receptacle of the protecting sleeve may comprise mutually engaging locking features.

For mounting and removing a disposable needle assembly to the distal end of the housing of the drug delivery device, the protective needle cap can be effectively used. Attachment of the needle assembly to the drug delivery device may be governed and controlled by the protective needle cap mounted thereon. In a similar way, also removal of a used needle assembly from the drug delivery device may be conducted or supported by the protective needle cap to be releasably and removably mounted to the receptacle of the protecting sleeve.

In a further embodiment, the drug delivery device also comprises a cartridge at least partially filled with the medicament and being arranged in the housing. The drug delivery device is particularly operable to individually set and to dispense a dose of the medicament. Moreover, the drug delivery device is particularly designed as an all mechanically implemented injection device of e.g. pen-injector type.

The drug delivery device may be of disposable type or of reusable type. If designed as a disposable device, the entire drug delivery device is intended to be discarded once the medicament contained in the cartridge has been used up. With a reusable device, the housing of the device may be opened or disassembled to replace an empty cartridge by a filled one.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39), des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, a preferred embodiment of the invention will be described by making reference to the drawings, in which.

DETAILED DESCRIPTION

Figure 1:
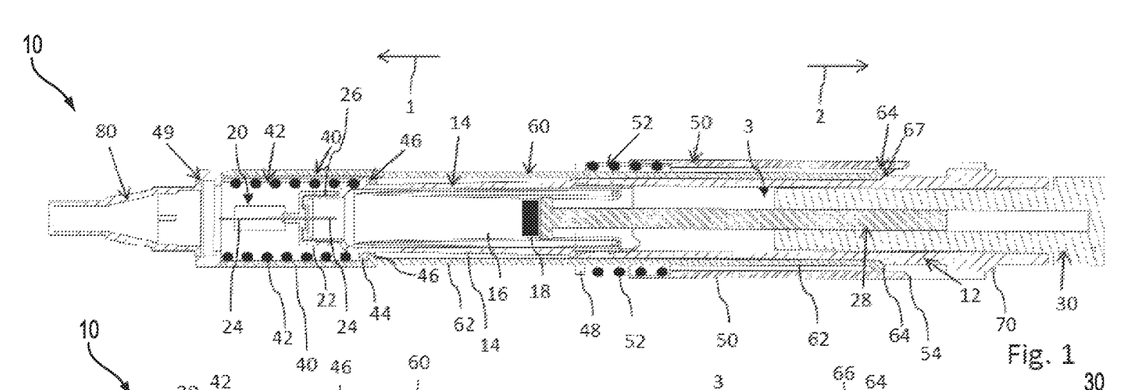
FIG. 1 schematically illustrates a longitudinal cross-section through a drug delivery device in an initial configuration.
Figure 2:
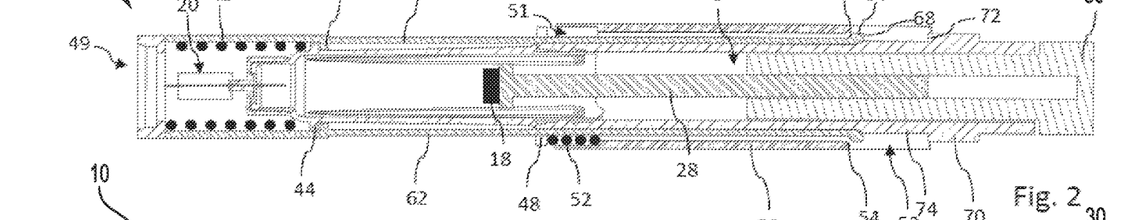
FIG. 2 shows the drug delivery device according to FIG. 1 with an interlocking member in a release position.
Figure 5:
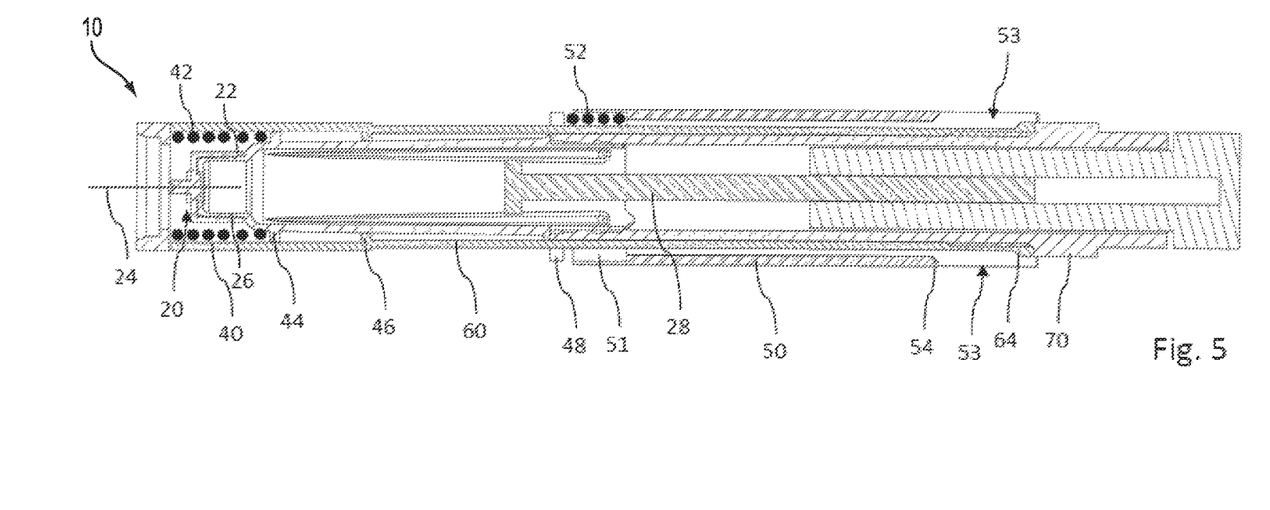
FIG. 5 shows the drug delivery device according to FIGS. 1 and 2 with the protecting sleeve in a retracted proximal stop position.

In the various cross-sections according to FIGS. 1, 2 and 5 a drug delivery device 10 in form of a pen injector is shown. The drug delivery device 10 comprises a housing 12, 14 to accommodate a cartridge 16 in a distal section and to accommodate a drive mechanism 3 in a proximal end section. The cartridge 16 comprises a tubular-shaped barrel which is sealed in proximal-direction 2 by means of a piston 18. The piston 18 is slidably disposed in the barrel of the cartridge 16 to expel a predefined amount of the medicament contained therein via a needle assembly 20 attached to a distal end of the distal housing component 14, which serves as a cartridge holder.

As illustrated for instance in FIGS. 1 and 2, the distal end section of the cartridge holder 14 comprises a threaded socket 26 to threadedly engage with a hub 22 of a disposable and non-shielded needle assembly 20. The needle assembly 20 further comprises a double-tipped needle 24. A proximal end of the needle 24 is adapted to penetrate a distally-located seal, e.g. a septum of the cartridge 16 in order to provide a liquid-transferring access to the interior volume of the cartridge 16.

As further illustrated in FIG. 1, the needle assembly 20 is originally provided with a protective cap 80. Originally, the needle hub 22 together with the injection needle 24 is sealed inside the protective cap 80. By means of the protective cap 80, the needle assembly 20 can be mounted to and removed from the distal end of a cartridge holder 14.

The proximally located housing 12 serves as a body of the drug delivery device 10. The body 12 therefore serves to accommodate a drive mechanism 3, which at least comprises a piston rod 28 to operably engage with the piston 18 of the cartridge 16. Moreover, the drive mechanism 3 comprises a dose setting and/or dose dispensing arrangement 30, by way of which the size of a dose of the medicament to be dispensed can be individually set and subsequently dispensed, e.g. by dialling or rotating a respective dose dial member and by depressing a dose button, typically located at a proximal end of the dose setting and dispensing arrangement 30 in distal-direction 1.

The drug delivery device 10 further comprises a protection mechanism in order to shield the needle assembly 20 when the device 10 is not in dose dispensing mode. The protection mechanism comprises a protecting sleeve 40 slidably attached to the distal end of the housing 14 to enclose the needle assembly 20 in a distal stop position. By comparing the configurations according to FIGS. 1 and 5 it is apparent, that the protecting sleeve 40 can be displaced from a distal stop position as illustrated in FIG. 1 into a retracted proximal stop position as shown in FIG. 5, wherein the distal end of the tipped needle 24 is exposed and extends in distal direction 1 beyond a distally located receptacle 49 of the protecting sleeve 40.

Additionally, the protection mechanism comprises an interlocking member 50 featuring a gripping sleeve, which is slidably disposed in axial-direction on the outer circumference of the proximal portion of the housing 12. As becomes for instance apparent by a comparison of FIGS. 1 and 2, the sleeve-like interlocking member 50 can be displaced in distal-direction 1 relative to the body or housing 12 of the drug delivery device 10 against the action of a locking spring element 52. The locking spring element 52 extends in axial-direction into a receptacle 51 provided at a distal end of the interlocking member 50.

An opposite distal end of the locking spring element 52 axially abuts against a radially outwardly extending protrusion or flange portion 48 of the housing 12. In this way, the interlocking member 50 can be displaced in distal-direction 1 relative to the housing 12 against the action of the locking spring element 52. Similarly also the protecting sleeve 40 is spring biased with respect to a distal portion 14 of the housing of the drug delivery device 10. As illustrated for instance in FIG. 1, a compression-type protecting spring element 42 extends axially inside the protecting sleeve 40.

The protecting spring element 42 axially abuts against a radially outwardly extending portion of the distally located receptacle 49 of the protecting sleeve 40. An opposite, hence proximal end of the protecting spring element 42 axially abuts with a radially outwardly extending flange portion 44 provided on the cartridge holder 14 of the housing of the drug delivery device 10.

Additionally, the protecting sleeve 40 comprises a radially inwardly extending flange portion 46 adapted to axially abut with a proximal end face of the flange portion 44. In this way, distally-directed displacement of the protecting sleeve 40 relative to the cartridge holder 14 can be limited and confined.

By means of the protecting spring element 42 and its arrangement inside the protecting sleeve 40, the protecting sleeve 40 can be displaced in proximal direction 2 relative to the housing 12, 14 of the drug delivery device 10 against the action of the protecting spring element 42. In other words, the housing 12, 14 of the drug delivery device 10 can be displaced in distal direction 1 relative to the protecting sleeve 40 to expose the needle assembly 20 against the action of the protecting spring element 42.

Such distally-directed displacement of the housing 12, 14 relative to the protecting sleeve 40 is effectively blocked as long as the interlocking member 50 is located in its proximal locking position as illustrated in FIG. 1. The protecting sleeve 40 comprises two diametrically oppositely-located slab-like extensions 60, 62 which extend in proximal-direction 2 almost through the entire interlocking member 50. At their proximal end, the extensions 60, 62 comprise radially outwardly extending protrusion 64, which in locking position of the interlocking member 50 are radially constrained by the inner sidewall of the interlocking member.

Moreover and as illustrated in FIGS. 1 and 2, the extensions 60, 62 axially abut with a radially widened stepped portion 74 of the proximal housing 12 of the drug delivery device 10. In this way, a distally-directed displacement of the housing 12, 14 relative to the interlocking member 50 remains substantially effectless.

Protecting sleeve 40 and housing 12, 14 of the drug delivery device 10 remain substantially axially fixed with respect to each other. It is only due to a distally-directed displacement of the interlocking member 50 against the action of the locking spring element 52 that the radially outwardly extending protrusion 64 of the two extensions 60, 62 are radially released as illustrated in FIG. 2.

Such a releasing displacement of the interlocking member 50 can be easily attained in the course of an injection procedure, wherein the distal end of the protecting sleeve 40 is pushed against the skin of a patient and wherein a distally-directed application force is exerted onto the sleeve-like interlocking member 50.

Once the release position of the interlocking member 50 as illustrated in FIG. 2 has been reached, the inclined ramp portion 67 located at a proximal and radially inwardly facing portion of the extensions 60, 62 may engage with a correspondingly shaped inclined portion 76 of the housing 12. In this way, a distally directed thrust acting on the housing 12 may lead to a radially outwardly directed displacement of the tongue-like extension 60, 62. As a consequence, the housing 12, 14 as a whole may be displaced in distal-direction 1 relative to the protecting sleeve 40 and relative to its extension 60, 62 until a further axial abutment of a proximal stop face 68 of the extension 60, 62 and a proximally-directed end face 72 of a radially outwardly extending rim 70 of the housing 12 has been reached.

The mutual engagement of the stop face 68 and the stop face 72 thereby defines the retracted stop position of the protecting sleeve 40 relative to the housing 12, 14.

It is of particular benefit, that distally-directed displacement of the housing 12, 14 relative to the protecting sleeve 40 can be attained via the interlocking member 50. The distally directed force applied by a user initially serves to displace the interlocking member 50 against the action of the locking spring element 52 in distal-direction 1. Once the spring element 52 is substantially compressed as shown in FIG. 2, a further force effect acting on the interlocking member 50 in distal-direction 1 equally transfers via the radially outwardly extending flange portion 48 to the housing 12, 14 of the drug delivery device 10, thereby inducing the radially outwardly-directed evasive movement of the proximal end of the extension 60, 62 and a corresponding distally-directed displacement of the housing 12, 14 together with the needle assembly 20 relative to the protecting sleeve 40.

Once the application force drops below a predefined threshold, typically at the end of a dispensing procedure, the protecting sleeve 40, the housing 12, 14 and the interlocking member 50 will return to their initial positions as shown in FIG. 1 under the effect of the two spring elements 42, 52. It is of particular benefit, when the protecting spring element 42 comprises a larger spring constant compared to the locking spring element 52. In this way, the protecting sleeve 40 will initially return into its distal stop position under the effect of the protecting spring element 42. At the end of this particular movement, another radially outwardly extending inclined portion 66 at a distal end face of the protrusion 64 of the extension 60, 62 engages with a correspondingly-shaped inclined portion 54 of the housing 12 in order to displace the free end of the extension 60, 62 radially inwardly, so that the free and proximal end of the extension 60, 62 can be constrained radially between the interlocking member 50 and the proximal housing component 12.

Figure 3:
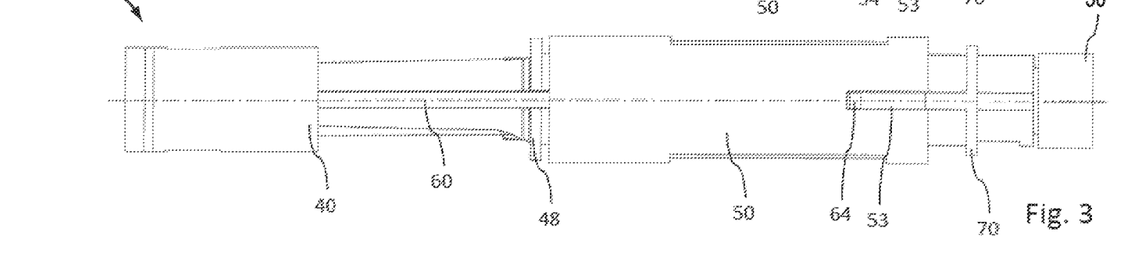
FIG. 3 shows a side view of the device according to FIG. 2, FIG. 4 schematically shows an enlarged section of the illustration according to FIG. 2.
Figure 4:
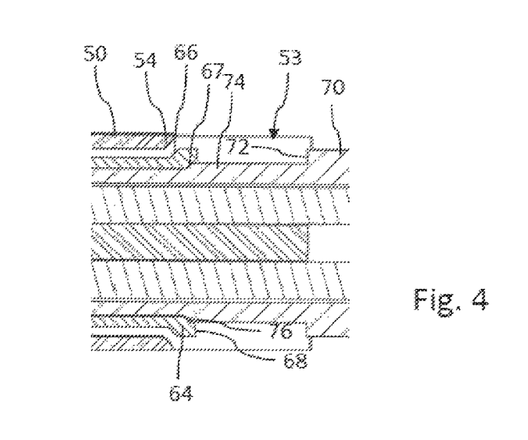
Figure 6:
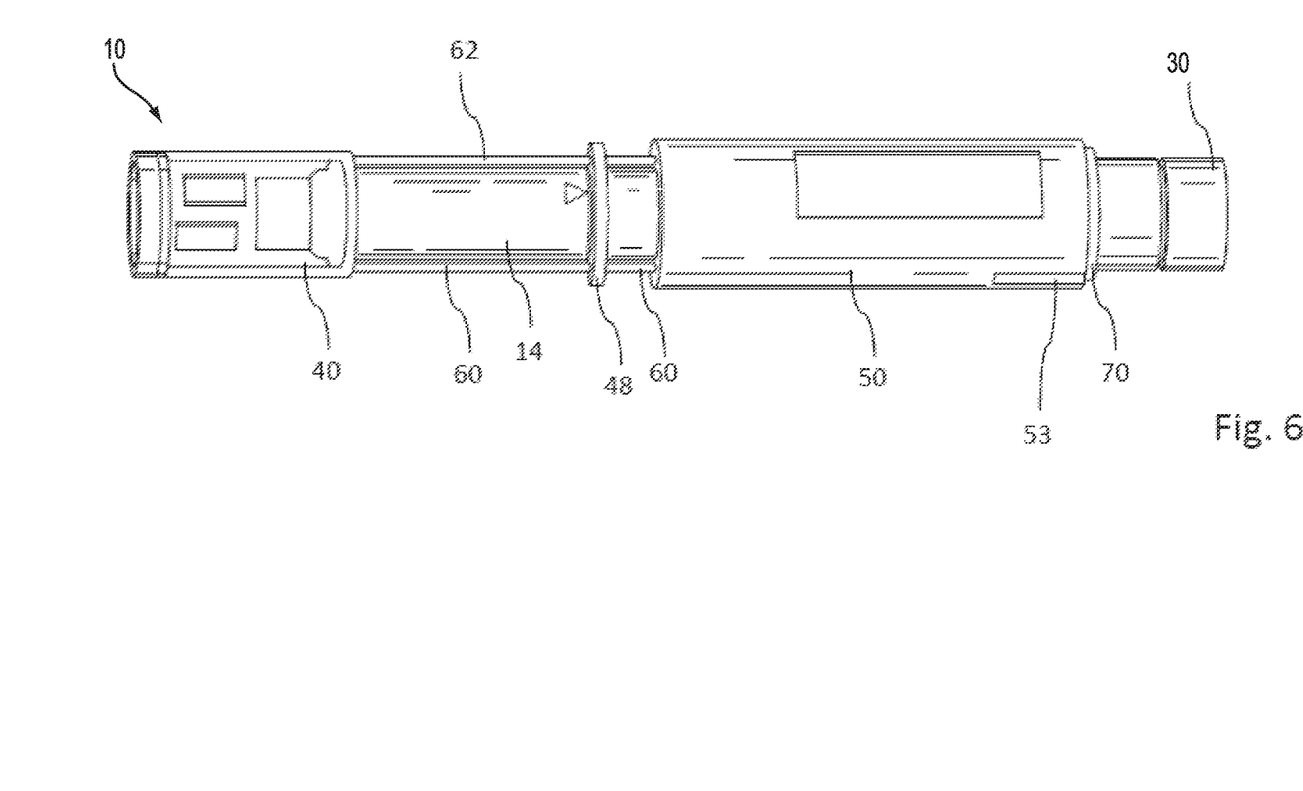
FIG. 6 shows another side view of the drug delivery device that corresponds to the device configuration according to FIG. 1.

As further indicated in FIGS. 3 and 6 interlocking member 50 may comprise and axially extending slit or groove 53 to receive the radially outwardly extending protrusion 64 of the extension 60, 62. As becomes further apparent from FIGS. 3 and 6, the extension 60, 62 axially extend through the circumference flange portion 48 of the housing 12.

Even though not particularly illustrated in the Figures, the protecting sleeve 40 together with the interlocking member 50 could also be implemented with a reusable drug delivery device. In such an embodiment the extensions 60, 62 could be at least temporally disassembled or disconnected from the housing 12 and/or from the cartridge holder 14 in order to allow disassembling of the cartridge holder 14 from the housing. In particular, the extensions 60, 62 may be split or bended radially outwardly to provide access to the cartridge holder 14. The cartridge holder 14 may then for instance be unscrewed from the housing 12, thereby allowing replacement of an empty cartridge.

It is further to be mentioned, that the distal end face of the protecting sleeve 40 comprises a receptacle 49 to releasably engage with a protective cap 80 of the needle assembly 20. In this way, the needle assembly 20 can be mounted and removed to the threaded portion 26 of the cartridge holder 14 with the protective cap 80 located thereon. In this way, danger of a stitch can be minimised during needle attachment and needle removal.

The invention claimed is:

1. A drug delivery device for dispensing of a dose of a medicament, the drug delivery device comprising:
an elongated housing extending in an axial direction, a distal section of the elongated housing accommodating a cartridge containing the medicament to be dispensed, the cartridge comprising a distally-located pierceable seal and a proximally located piston,
wherein the elongated housing is adapted to detachably support a needle assembly at a distal end of the elongated housing,
a drive mechanism comprising a piston rod to operably engage with the piston of the cartridge,
a protecting sleeve slidably attached to the distal end of the elongated housing to enclose the needle assembly in a distal stop position and to expose the needle assembly in a retracted proximal stop position,
an interlocking member operably engaged with the protecting sleeve and being slidably and axially displaceable relative to the elongated housing on an outer circumference of the elongated housing between a proximal locking position, in which the protecting sleeve is locked to the elongated housing, and a distal release position, in which the protecting sleeve is axially displaceable relative to the elongated housing, and
a locking spring element having one end in axial abutment with a distally facing abutment of the interlocking member and having an opposite end in axial abutment with the elongated housing, wherein the interlocking member is displaceable in a distal direction relative to the elongated housing in opposition to a force exerted on the interlocking member by the locking spring element.

2. The drug delivery device according to claim 1, wherein the interlocking member comprises a gripping sleeve slidably attached to the elongated housing.

3. The drug delivery device according to claim 1, wherein the proximal locking position of the interlocking member coincides with a proximal stop position of the interlocking member and wherein the distal release position of the interlocking member coincides with a distal stop position of the interlocking member.

4. The drug delivery device according to claim 1, wherein the protecting sleeve is displaceable in a proximal direction relative to the elongated housing in opposition to a force exerted on the protecting sleeve by a protecting spring element.

5. The drug delivery device according to claim 4, wherein a spring constant of the locking spring element is substantially smaller than a spring constant of the protecting spring element.

6. The drug delivery device according to claim 1, wherein the protecting sleeve comprises at least one extension extending in a proximal direction, and wherein the at least one extension has a radially outwardly extending protrusion.

7. The drug delivery device according to claim 6, wherein the at least one extension extends radially between the elongated housing and the interlocking member.

8. The drug delivery device according to claim 6, wherein the at least one extension axially abuts a stepped portion of the elongated housing and is radially constrained by the interlocking member when the interlocking member is in the proximal locking position.

9. The drug delivery device according to claim 8, wherein the at least one extension is radially released to pass by the stepped portion when the interlocking member is in the release position.

10. The drug delivery device according to claim 6, wherein the radially outwardly extending protrusion comprises at least one inclined ramp portion.

11. The drug delivery device according to claim 6, wherein the radially outwardly extending protrusion comprises a proximal end face to axially abut a correspondingly shaped radially outwardly extending rim of the elongated housing.

12. The drug delivery device according to claim 6, wherein the radially outwardly extending protrusion of the at least one extension is axially guided in a slit or in a groove of the interlocking member.

13. The drug delivery device according to claim 1, wherein a distal end of the protecting sleeve comprises a receptacle to removably receive a protective needle cap of the needle assembly.

14. The drug delivery device of claim 1, wherein the distally located pierceable seal of the cartridge comprises a pierceable septum.

15. The drug delivery device of claim 1, wherein the needle assembly comprises a double-tipped needle.

16. The drug delivery device of claim 15, wherein a proximal needle of the double-tipped needle is adapted to penetrate the distally located pierceable seal of the cartridge in order to provide a liquid transferring access to an interior volume of the cartridge.

17. The drug delivery device of claim 1, wherein the distal section of the elongated housing comprises a threaded socket to threadedly engage a hub of the needle assembly.

18. The drug delivery device according to claim 1, wherein the protecting sleeve is interlocked with the elongated housing when in the distal stop position and wherein the protecting sleeve becomes axially displaceable relative to the elongated housing by an axial displacement of the interlocking member relative to the elongated housing.

19. A drug delivery device for dispensing of a dose of a medicament, the drug delivery device comprising:
an elongated housing having a distal end and extending in an axial direction to accommodate a cartridge containing the medicament to be dispensed, the elongated housing being adapted to detachably support a needle assembly at the distal end, a drive mechanism comprising a piston rod to operably engage with a piston of the cartridge, a protecting sleeve slidably attached to the distal end of the elongated housing to enclose the needle assembly in a distal stop position and to expose the needle assembly in a retracted proximal stop position, an interlocking member operably engaged with the protecting sleeve and axially displaceable relative to the elongated housing between a locking position, in which the protecting sleeve is locked to the elongated housing, and a release position, in which the protecting sleeve is axially displaceable relative to the elongated housing, and a locking spring element having one end in axial abutment with a distally facing abutment of the interlocking member and having an opposite end in axial abutment with the elongated housing;

wherein the interlocking member is displaceable in a distal direction relative to the elongated housing, wherein the protecting sleeve is displaceable in a proximal direction relative to the elongated housing in opposition to a force exerted on the protecting sleeve element by a protecting spring element, and wherein a spring constant of the locking spring element is substantially smaller than a spring constant of the protecting spring element.

* * * * *